US008188096B2

(12) United States Patent
Watterson et al.

(10) Patent No.: US 8,188,096 B2
(45) Date of Patent: *May 29, 2012

(54) PROTEIN KINASE TARGETED THERAPEUTICS

(75) Inventors: D. Martin Watterson, Chicago, IL (US); Linda J. Van Eldik, Chicago, IL (US)

(73) Assignee: Northwestern University, Evanston, IL (US)

(*) Notice: Subject to any disclaimer, the term of this patent is extended or adjusted under 35 U.S.C. 154(b) by 6 days.

This patent is subject to a terminal disclaimer.

(21) Appl. No.: 13/034,411

(22) Filed: Feb. 24, 2011

(65) Prior Publication Data

US 2011/0166153 A1 Jul. 7, 2011

Related U.S. Application Data

(63) Continuation of application No. 12/566,153, filed on Sep. 24, 2009, now Pat. No. 7,919,485, which is a continuation of application No. 11/833,152, filed on Aug. 2, 2007, now abandoned.

(60) Provisional application No. 60/834,962, filed on Aug. 2, 2006.

(51) Int. Cl.
C07D 239/42 (2006.01)

(52) U.S. Cl. .................................... 514/256

(58) Field of Classification Search .................. 514/256
See application file for complete search history.

(56) References Cited

U.S. PATENT DOCUMENTS

| 4,355,029 A | 10/1982 | Ridolfo |
| 4,590,194 A | 5/1986 | Lesher |
| 4,623,376 A | 11/1986 | Speltz |
| 7,452,887 B2 | 11/2008 | Dickson |
| 2005/0130954 A1 | 6/2005 | Mitchell |

FOREIGN PATENT DOCUMENTS

| WO | 2006/050389 | 11/2006 |

OTHER PUBLICATIONS

Kyriakis JM and Avruch J "Mammalian Mitogen-Activated Protein Kinase Signal Transduction Pathways Activated by Stress and Inflammation" Physiol Rev (2001) 81: 808-869.
Bonni A, et al., "Cell Survival Promoted by theRas-MAPK Signaling Pathway by Transcription-Dependent and-Independent Mechanisms," Science. Nov. 12, 1999;286(5443):1358-62.
Chadee DN, "Direct Activation of Mitogen-Activated Protein Kinase Kinase Kinase MEKK1 by the Ste20p Homologue GCK and the Adapter Protein TRAF2" Mol Cell Biol. Feb. 2002;22(3):737-49.
Chang L, et al., "Mammalian MAP kinase signalling cascades," Nature Mar. 1, 2001;410(6824):37-40.
Chen YR, et al., "Mammalian c-Jun N-terminal kinase pathway and STE20-related kinases," Gene ther mol biol, Dec. 1999vol 4, 83-98.

Hazzalin CA, et al., "MAPK-Regulated Transcription: A Continuously Variable Gene Switch?," Nat Rev Mol Cell Biol. Jan. 2002;3(1):30-40.
Kato Y, et al., "BMK1/ERK5 regulates serum-induced early gene expression through transcription factor MEF2C," EMBO J. Dec. 1, 1997;16(23):7054-66.
Kiefer F, et al., "HPK1, a hematopoietic protein kinase activating the SAPK/JNK pathway," EMBO J. Dec. 16, 1996;15(24):7013-25.
Pearson G, et al., "ERK5 and ERK2 Cooperate to Regulate NF-kB and Cell Transformation," J Biol Chem. Mar. 16, 2001;276(11):7927-31.
Weston CR, et al., "MAP Kinase Signaling Specificity," Science. Jun. 28, 2002;296(5577):2345-7.
Kaminska B "MAPK signalling pathways as molecular targets for anti-inflammatory therapy—from molecular mechanisms to therapeutic benefits," (2005) Biochim Biophys Acta 1754: 253-262.
Kumar S, et al., "P38 MAP Kinases: Key Signalling Molecules As Therapeutic Targets for Inflammatory Diseases," Nature Rev Drug Discovery 2: 717-726.
Saklatvala J "The p38 MAP kinase pathway as a therapeutic target in inflammatory disease," (2004) Curr Opin Pharmacol 4: 372-377.
Engelberg D , "Stress-activated protein kinases—tumor suppressors or tumor initiators?" (2004) Sem Cancer Biol 14: 271-282.
Rennefahrt U, et al., "Stress kinase signaling in cancer: fact or fiction?," (2005) Cancer Lett 217: 1-9.
Schieven GL "The Biology of p38 Kinase: A Central Role in Inflammation," (2005) Curr Topics Med Chem 5: 921-928.
Jinlian L "p38 MAPK in regulating cellular responses to ultraviolet radiation," (2007) J Biomed Sci 14: 303-312.
Platanias LC "Review in Translational Hematology: Map kinase signaling pathways and hematologic malignancies" (2003) Blood 101: 4667-4679.
Knippschild U, et al., "The role of the casein kinase 1 family: participation in multiple cellular processes in eukaryotes," 2005, Cellular Signalling 17: 675-689.
Knippschild U et al., 2005 "The Role of Casein Kinase 1 (CK1) Family in Different Signaling Pathways Linked to Cancer Development," ONKOLOGIE 28: 508-514.
Ricchi et al., "Nonsteroidal Anti-Inflammatory Drugs in Colorectal Cancer: From Prevention to Therapy." British Journal of Cancer 2003, vol. 88; p. 806. Tamayo et al., "Design and sythesis of potent pyridazine inhibitors of p38 MAP kinase' Bioorganic and Medicinal Chemistry Letter," (2005) vol. 15, p. 2409-2413.
International Search Report and Written Opinion from related International Patent Application No. PCT/US07/17375, Jul. 18, 2008.
Stella, et al., Prodrugs: Challenges and Rewards, Part 1: Biotechnology: Pharmaceutical Aspects, p. 24 (2007).

Primary Examiner — Brandon Fetterolf
Assistant Examiner — Christopher R Stone
(74) Attorney, Agent, or Firm — Casimir Jones SC

(57) ABSTRACT

The present invention relates to compositions and methods useful in treating diseases and disorders related to protein kinases. In particular, the present invention relates to compositions and methods useful for targeting protein kinases related to mitogen activated protein kinase (MAPK) pathways (e.g., p38 MAPK, JNK, ERK, and upstream and downstream protein kinases) and/or casein kinase (CK) pathways (e.g., CK1δ, and upstream and downstream protein kinases), and diseases and disorders related to MAPK pathways (e.g., p38 MAPK, JNK, ERK, and upstream and downstream protein kinases) and/or CK pathways (e.g., CK1δ, and upstream and downstream protein kinases).

2 Claims, 4 Drawing Sheets

SCHEME II:

Synthesis of precursor and example of two amines

Scheme 1: Reagents and conditions (i) LDA, THF, -78°C; (ii) 60% NaH, THF, 0°C, 45 min then ethyl bromoacetate, rt, 18 h; (iii) N2H4, ethanol, reflux, 9hr ; (iv) Br$_2$, AcOH, 95 °C, 4 h; (v) POCl3, 90°C, 2 h; (vi) amine, Butanol, 130° C, 21hrs.

Figure 2.

Example of *in vitro* protein kinase inhibition by compound

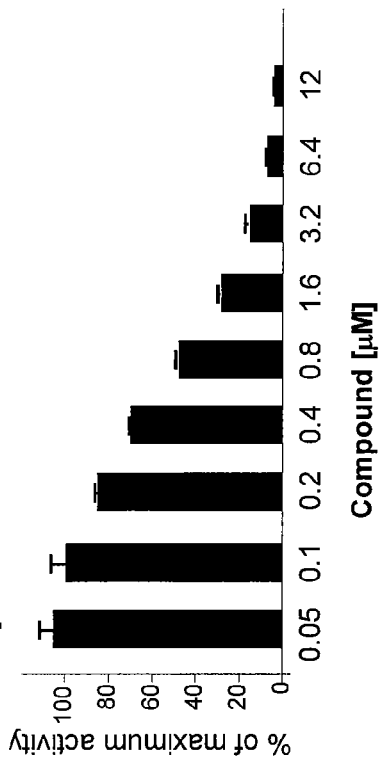

A. p38α MAPK inhibition

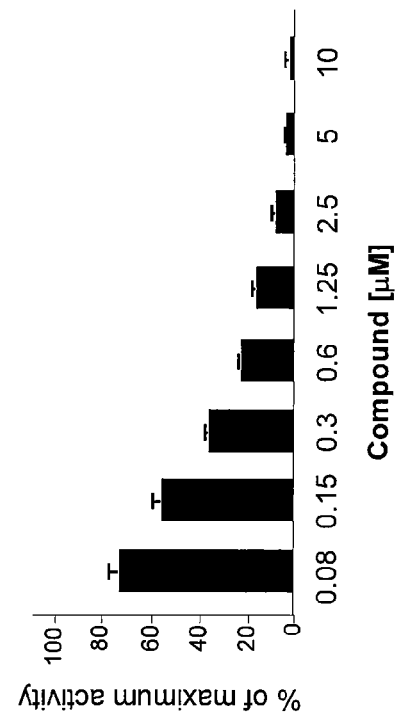

B. CK1δ inhibition

Compound inhibits p38α MAPK (panel A) or CK1δ (panel B) enzyme activity in a concentration-dependent manner. The *in vitro* phosphorylation of a standard protein or peptide substrate by purified human p38α MAPK or CK1δ was measured in the presence of 100 μM ATP, in the absence or presence of increasing concentrations of compound. Data are expressed as percent of the maximal enzyme activity, where enzyme activity in the absence of compound is taken as 100%.

Example of compound (cmpd) attenuation of stressor-induced (Injury; Inj) serum cytokine levels

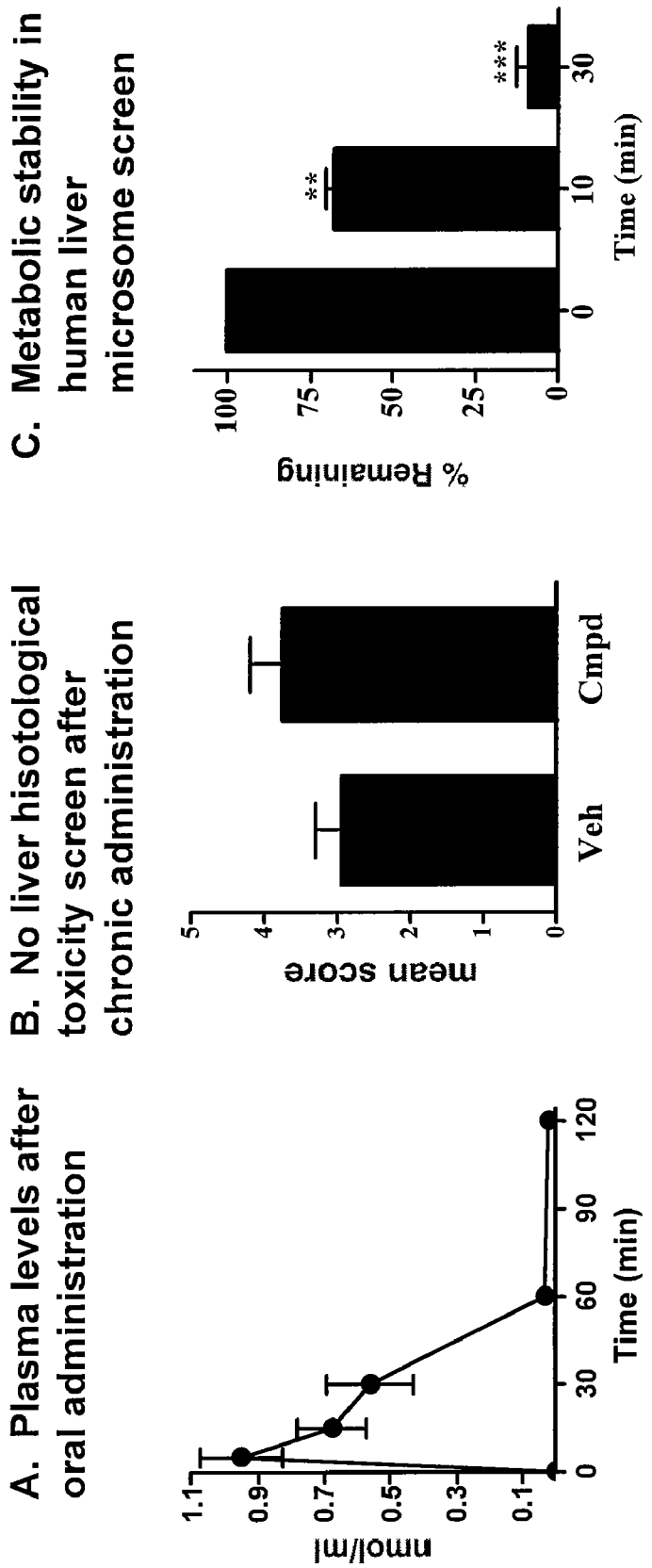

PROTEIN KINASE TARGETED THERAPEUTICS

CROSS-REFERENCE TO RELATED APPLICATIONS

The present application is a continuation of allowed U.S. patent application Ser. No. 12/566,153, filed Sep. 24, 2009, which is a continuation of abandoned U.S. patent application Ser. No. 11/833,152, filed Aug. 2, 2007, which claims priority to expired U.S. Provisional Application No. 60/834,962, filed Aug. 2, 2006, the contents of which are herein incorporated by reference in their entireties.

STATEMENT REGARDING FEDERALLY SPONSORED RESEARCH OR DEVELOPMENT

This invention was made with government support under Grant No. NS 047586 awarded by the National Institutes of Health. The government has certain rights in the invention.

FIELD OF THE INVENTION

The present invention relates to compositions and methods useful in treating diseases and disorders related to protein kinases. In particular, the present invention relates to compositions and methods useful for targeting protein kinases related to mitogen activated protein kinase (MAPK) pathways (e.g., p38 MAPK, JNK, ERK, and upstream and downstream protein kinases) and/or casein kinase (CK) pathways (e.g., CK1δ, and upstream and downstream protein kinases), and diseases and disorders related to MAPK pathways (e.g., p38 MAPK, JNK, ERK, and upstream and downstream protein kinases) and/or CK pathways (e.g., CK1δ, and upstream and downstream protein kinases).

BACKGROUND OF THE INVENTION

Intracellular protein kinases related to MAPK (e.g., p38 MAPK; JNK, ERK) and CK (e.g., CK1δ) are part of signal transduction pathways activated by stress and represent desirable therapeutic targets, especially for inflammatory disorders and diseases (e.g., arthritis). Previous efforts to target (e.g., inhibit) intracellular protein kinases related to MAPK (e.g., p38 MAPK, JNK, ERK) and CK (e.g., CK1δ) have been met with failure, in that previous inhibitors have had problems either directly or indirectly related to a compound's molecular properties.

What are needed are compositions and methods that will effectively target protein kinases related to MAPK (e.g., p38 MAPK, JNK, ERK) and/or CK (e.g., CK1δ), that have minimal or no toxicological impact to the subject, and that can be useful as treatment and therapeutic options for diseases and disorders related to MAPK pathways (e.g., p38 MAPK, JNK, ERK) and/or CK pathways (e.g., CK1δ).

SUMMARY OF THE INVENTION

The present invention relates to compositions and methods useful in treating diseases and disorders related to protein kinases. In particular, the present invention relates to compositions and methods useful for targeting protein kinases related to mitogen activated protein kinase (MAPK) pathways (e.g., p38 MAPK, JNK, ERK, and upstream and downstream protein kinases) and/or casein kinase (CK) pathways (e.g., CK1δ, and upstream and downstream protein kinases), and diseases and disorders related to MAPK pathways (e.g., p38 MAPK, JNK, ERK, and upstream and downstream protein kinases) and/or CK pathways (e.g., CK1δ, and upstream and downstream protein kinases). Novel inhibitors of protein kinases related to MAPK (e.g., p38 MAPK, JNK, ERK, and upstream and downstream protein kinases) and CK (e.g., CK1δ, and upstream and downstream protein kinases) are presented, and the molecular properties of these inhibitors allow them to be orally bioavailable for use in animal models and for human therapeutics alone or in combination with other therapeutic molecules.

In some embodiments, the compositions and methods of the present invention find use in research applications (e.g., drug screening, molecular and cellular based research, computer modeling scenarios).

In certain embodiments, the present invention provides compositions comprising one or more anti-inflammatory agents and a compound described by one or more of the following structures:

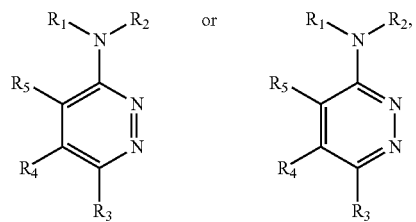

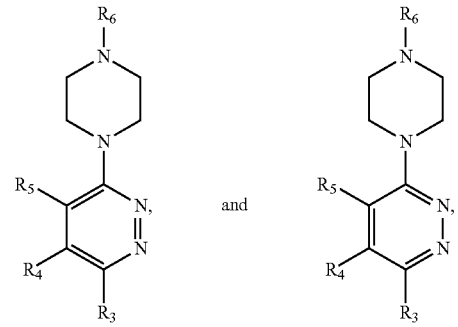

including salts and both R and S enantiomeric forms and racemic mixtures thereof; wherein R1, R2, R3, R4, and R6 are independently selected from H, C, CH, CH2, CH3

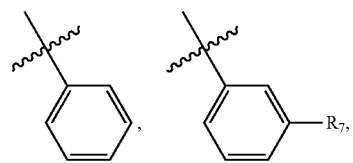

naphthalene,

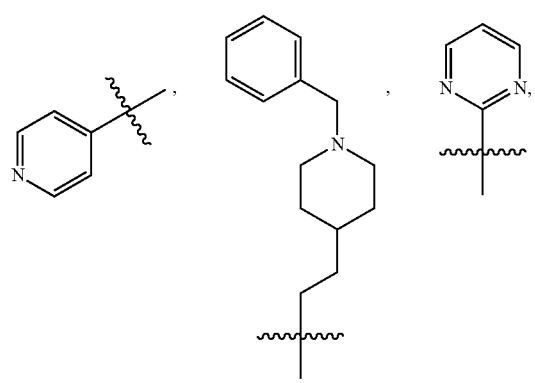

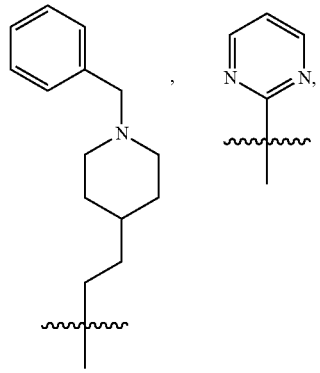

and a substituted or unsubstituted chemical moiety comprising at least one of the following: alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, carboxamide, hydrogen, amino, nitrogen, pyridine, quinoline, isoquinoline, pyrazine, quinoxaline, acridine, pyrimidine, quinazoline, pyridazine, piperazine, cinnoline, cycloaliphatic subgroup, ester, ether, sulfur, phosphorous, oxygen, an aromatic ring, a non-aromatic ring, a linear or branched, saturated or unsaturated, a substituted or unsubstituted, aliphatic chain having at least 2 carbons; wherein R5 is H, CH3, a linear or branched, saturated or unsaturated, a substituted or unsubstituted, aliphatic chain having less than 5 carbons; wherein R7 is selected from the group consisting of H, C, CH, CH2, CH3,

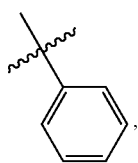

naphthalene, and a substituted or unsubstituted chemical moiety comprising at least one of the following: alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, carboxamide, hydrogen, amino, nitrogen, pyridine, quinoline, isoquinoline, pyrazine, quinoxaline, acridine, pyrimidine, quinazoline, pyridazine, piperazine, cinnoline, cycloaliphatic subgroup, ester, ether, sulfur, phosphorous, oxygen, an aromatic ring, a non-aromatic ring, a linear or branched, saturated or unsaturated, a substituted or unsubstituted, aliphatic chain having at least 2 carbons.

In some embodiments, R3 is aromatic and R4 is a substituted or unsubstituted amine.

In some embodiments, the size of the R5 group is such that it does not sterically hinder the R4 group.

In some embodiments, the compound is one or more of:

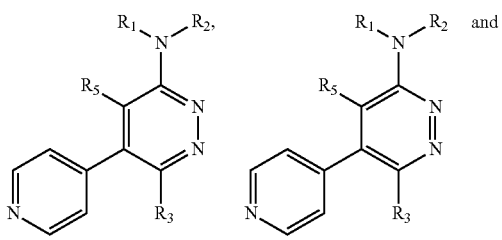

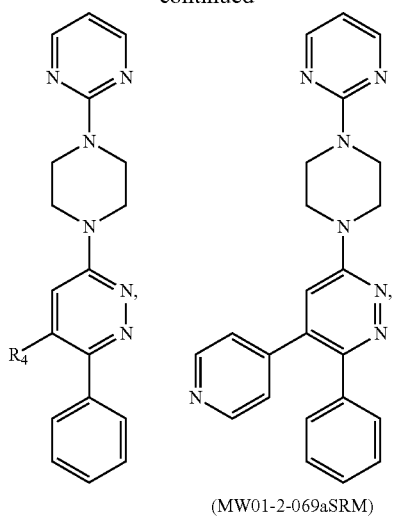

(MW01-2-069aSRM)

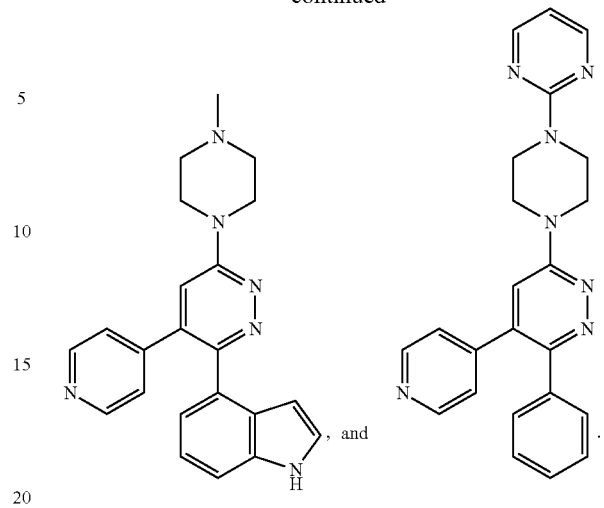

, and

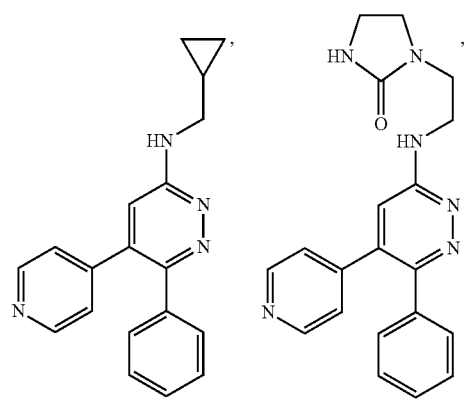

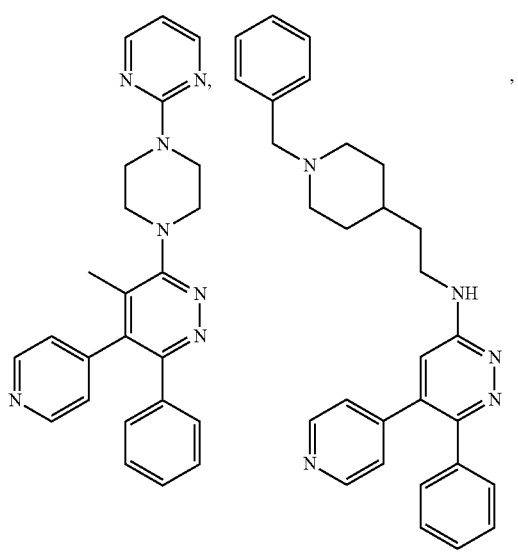

In some embodiments, the one or more anti-inflammatory agents include non-steroidal anti-inflammatory drugs (NSAIDs), anti-cytokines, imatinib mesylate, sorafenib, sunitinib malate, and anti-chemokines.

In some embodiments, the compound is an inhibitor of protein kinases related to MAPK pathways (e.g., p38 MAPK, JNK, ERK, and upstream and downstream protein kinases) and/or CK pathways (e.g., CK1δ, and upstream and downstream protein kinases).

In certain embodiments, the present invention provides compositions comprising one or more anti-inflammatory agents and a compound described by the following formula:

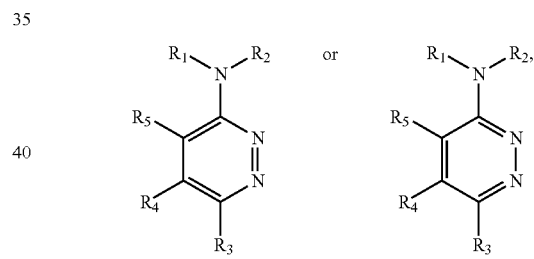

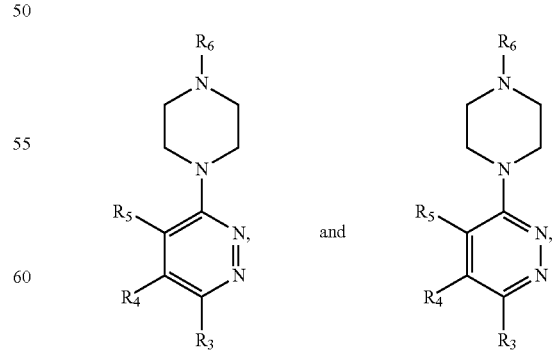

including salts and both R and S enantiomeric forms and racemic mixtures thereof; wherein R1, R2, R3, R4, and R6 are independently selected from H, C, CH, CH2, CH3,

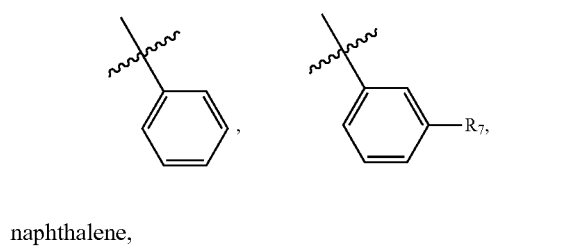

naphthalene,

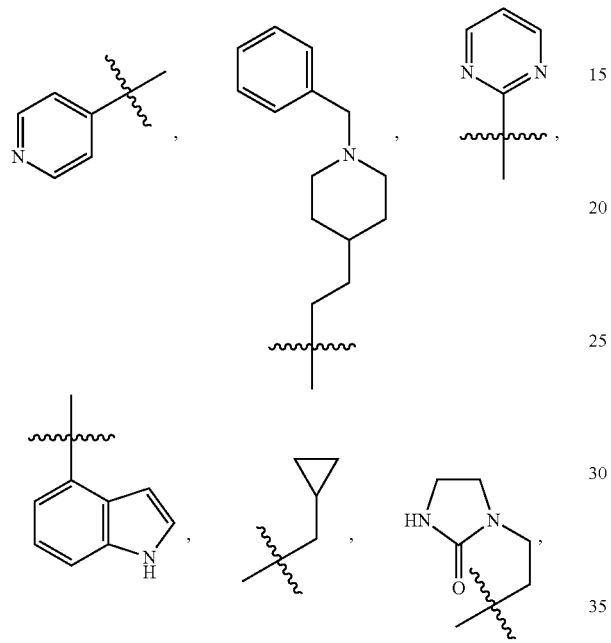

and a substituted or unsubstituted chemical moiety comprising at least one of the following: alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, carboxamide, hydrogen, amino, nitrogen, pyridine, quinoline, isoquinoline, pyrazine, quinoxaline, acridine, pyrimidine, quinazoline, pyridazine, piperazine, cinnoline, cycloaliphatic subgroup, ester, ether, sulfur, phosphorous, oxygen, an aromatic ring, a non-aromatic ring, a linear or branched, saturated or unsaturated, a substituted or unsubstituted, aliphatic chain having at least 2 carbons; wherein R5 is H, CH3, a linear or branched, saturated or unsaturated, a substituted or unsubstituted, aliphatic chain having less than 5 carbons; wherein R7 is selected from the group consisting of H, C, CH, CH2, CH3,

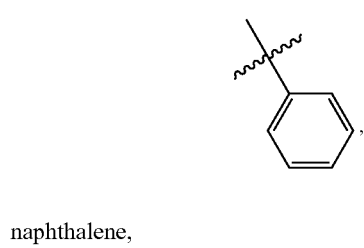

naphthalene, and a substituted or unsubstituted chemical moiety comprising at least one of the following: alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, carboxamide, hydrogen, amino, nitrogen, pyridine, quinoline, isoquinoline, pyrazine, quinoxaline, acridine, pyrimidine, quinazoline, pyridazine, piperazine, cinnoline, cycloaliphatic subgroup, ester, ether, sulfur, phosphorous, oxygen, an aromatic ring, a non-aromatic ring, a linear or branched, saturated or unsaturated, a substituted or unsubstituted, aliphatic chain having at least 2 carbons.

In some embodiments, R3 is aromatic and R4 is a substituted or unsubstituted amine.

In some embodiments, the size of the R5 group is such that it does not sterically hinder the R4 group.

In some embodiments, the compound is one or more of:

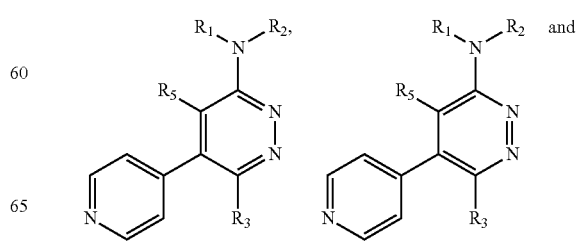

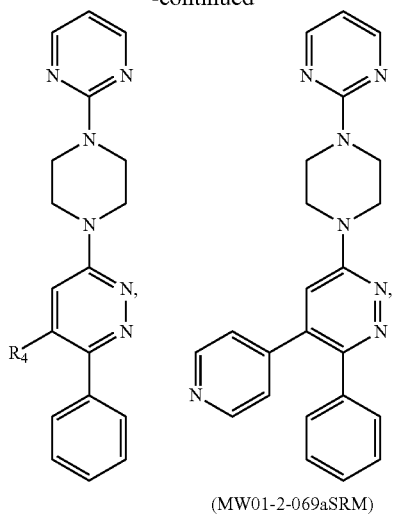

(MW01-2-069aSRM)

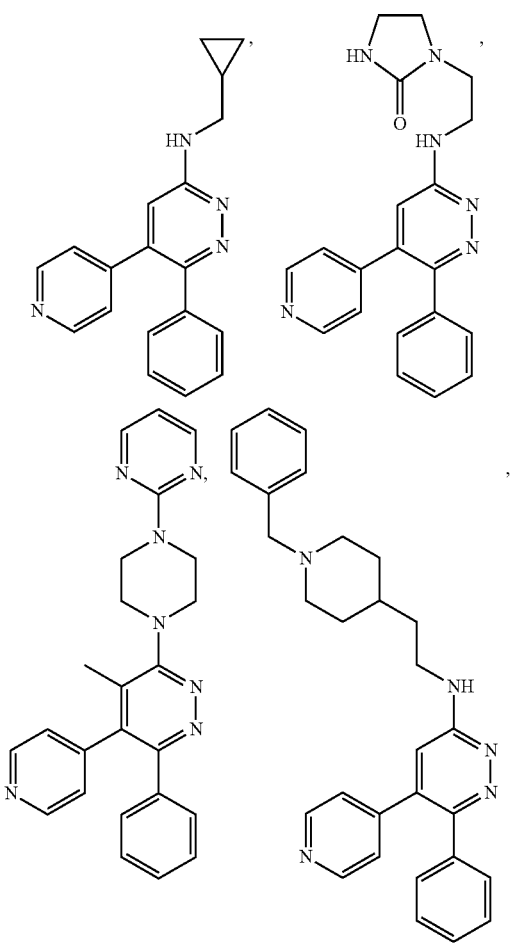

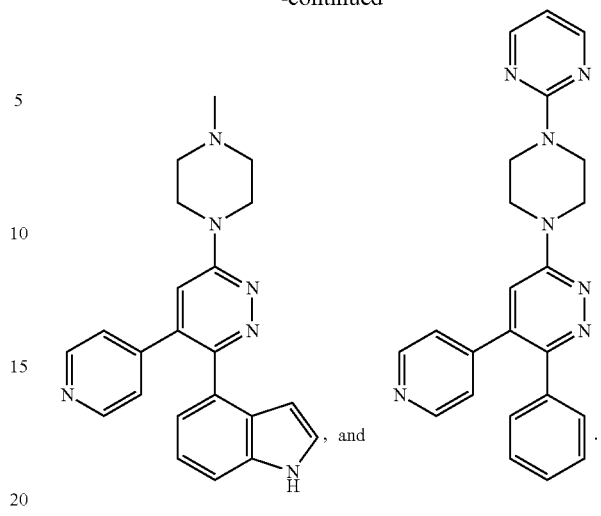

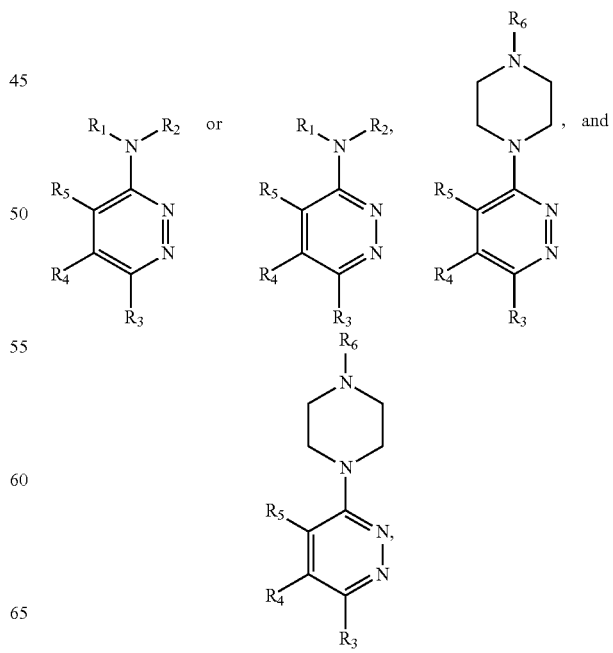

In some embodiments, the pharmaceutical composition comprises one or more anti-inflammatory agents including non-steroidal anti-inflammatory drugs (NSAIDs), anti-cytokines, imatinib mesylate, sorafenib, sunitinib malate, and anti-chemokines.

In some embodiments, the compound is an inhibitor of protein kinases related to MAPK pathways (e.g., p38 MAPK, JNK, ERK, and upstream and downstream protein kinases) and/or CK pathways (e.g., CK1δ, and upstream and downstream protein kinases).

In certain embodiments, the present invention provides methods for treating a disorder selected from the group consisting of a skin disorder, an intestinal disorder, a lung disorder, interstitial cystitis of the bladder, coronary disease after ischemia-reperfusion injury, acute renal inflammation, bacterial otitis media, chorioretinal vascular disease, a neurological disorder, aplastic anemia, bone marrow failure syndrome, and cancer, comprising administering an effective amount of a compound to a subject suffering from the disorder, wherein the compound comprises the following formula:

including salts and both R and S enantiomeric forms and racemic mixtures thereof; wherein R1, R2, R3, R4, and R6 are independently selected from H, C, CH, CH2, CH3,

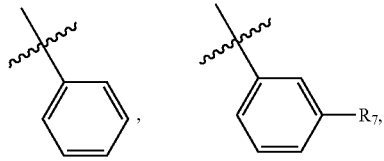

naphthalene,

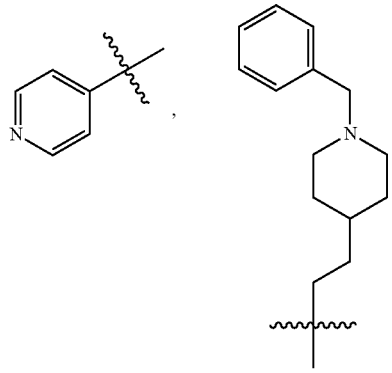

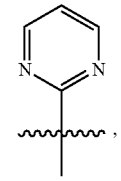

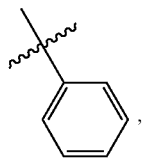

naphthalene,

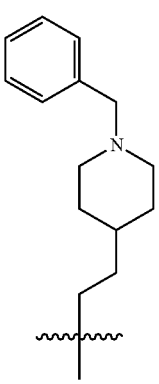

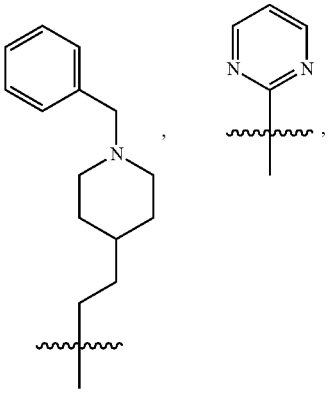

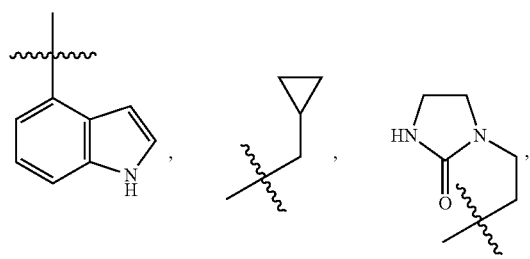

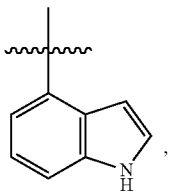

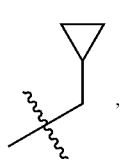

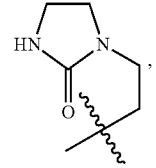

and a substituted or unsubstituted chemical moiety comprising at least one of the following: alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, carboxamide, hydrogen, amino, nitrogen, pyridine, quinoline, isoquinoline, pyrazine, quinoxaline, acridine, pyrimidine, quinazoline, pyridazine, piperazine, cinnoline, cycloaliphatic subgroup, ester, ether, sulfur, phosphorous, oxygen, an aromatic ring, a non-aromatic ring, a linear or branched, saturated or unsaturated, a substituted or unsubstituted, aliphatic chain having at least 2 carbons; wherein R5 is H, CH3, a linear or branched, saturated or unsaturated, a substituted or unsubstituted, aliphatic chain having less than 5 carbons; wherein R7 is selected from the group consisting of H, C, CH, CH2, CH3, and a substituted or unsubstituted chemical moiety comprising at least one of the following: alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfonyl, sulfenyl, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, carboxamide, hydrogen, amino, nitrogen, pyridine, quinoline, isoquinoline, pyrazine, quinoxaline, acridine, pyrimidine, quinazoline, pyridazine, piperazine, cinnoline, cycloaliphatic subgroup, ester, ether, sulfur, phosphorous, oxygen, an aromatic ring, a non-aromatic ring, a linear or branched, saturated or unsaturated, a substituted or unsubstituted, aliphatic chain having at least 2 carbons.

In some embodiments, R3 is aromatic and R4 is a substituted or unsubstituted amine.

In some embodiments, the size of the R5 group is such that it does not sterically hinder the R4 group.

In some embodiments, the compound is one or more of:

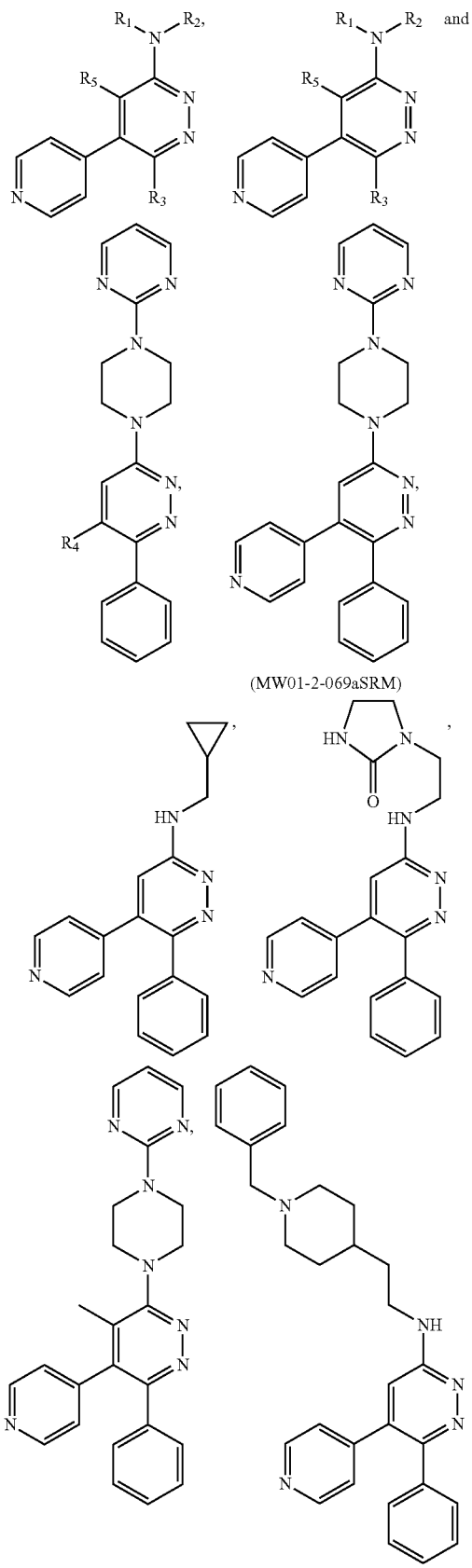

(MW01-2-069aSRM)

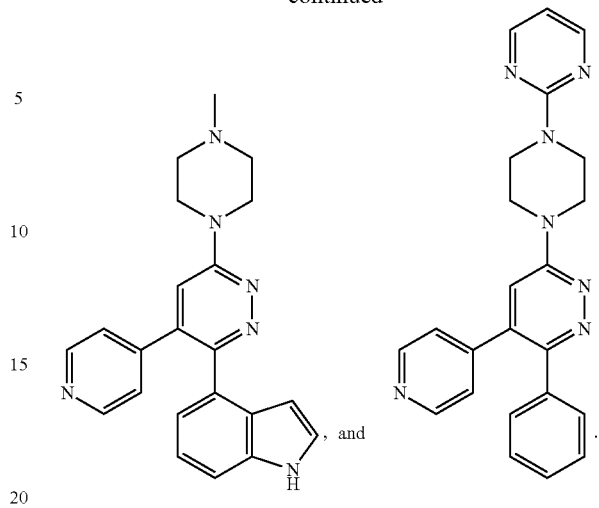

In some embodiments, the compound is an inhibitor of protein kinases related to MAPK pathways (e.g., p38 MAPK, JNK, ERK, and upstream and downstream protein kinases) and/or CK pathways (e.g., CK1δ, and upstream and downstream protein kinases).

In some embodiments, the methods result in prevention and/or a reduction of inflammation in the subject.

In some embodiments, the method further comprises administering an additional agent for treating the disorder (e.g., an agent for treating skin disorders, an agent for treating intestinal disorders, an agent for treating lung disorders, an agent for treating neurological disorders, an agent for treating cancer (e.g., including metastasis), an agent for treating interstitial cystitis of the bladder, an agent for treating coronary disease after ischemia-reperfusion injury, an agent for treating acute renal inflammation, an agent for treating bacterial otitis media, an agent for treating chorioretinal vascular disease, an agent for treating aplastic anemia, and an agent for treating bone marrow failure syndrome). In some embodiments, the agent is an anti-inflammatory agent such as nonsteroidal anti-inflammatory drugs (NSAIDs), anti-cytokines, imatinib mesylate, sorafenib, sunitinib malate, and anti-chemokines.

In some embodiments, the skin disorder is one or more of ichthyosis vulgaris, atopic dermatitis, psoriasis, eczema, allergic skin disease, and hypersensitivity reactions. In some embodiments, the intestinal disorder is one or more of inflammatory bowel disease, Crohn's disease, ulcers, bacterial infections, hemorrhagic shock, diarrhea, colitis, pancreatitis. In some embodiments, the lung disorder is one or more of acute lung injury after infection, sepsis, thrombin-induced lung injury, lung injury after reperfusion, chronic obstructive pulmonary disease, cystic fibrosis, inflammatory airway diseases. In some embodiments, the neurologic disorder is one or more of multiple sclerosis, Alzheimer's disease, vascular dementia, traumatic brain injury, ALS, Parkinson's disease, stroke, vasogenic brain edema, meningoencephalitis, cerebral hemorrhage, Guillain-Barre syndrome. In some embodiments, the cancer is prostate cancer, breast cancer, skin cancer, brain cancer, leukemia, lymphoma, and multiple myeloma. In some embodiments, the cancer is a metastasized cancer.

It should be understood that where different chemical constituents are described for any particular location on a chemical scaffold described herein, each of the possible combinations of constituents are contemplated herein.

DEFINITIONS

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, ayes, etc.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using the screening methods of the present invention. In some embodiments of the present invention, test compounds include antisense compounds.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like.

As used herein, the term "inflammatory condition" "inflammatory disorder" or similar term refers to a condition wherein the organism's immune cells are activated. Such a condition is characterized by an inflammatory response with pathologic sequelae. In some scenarios, the state is characterized by infiltration of mononuclear cells, proliferation of fibroblasts and small blood vessels, increased connective tissue, and tissue destruction. Examples of inflammatory diseases include, but are not limited to, arthritis (e.g., osteoarthritis, rheumatoid arthritis, etc.), inflammatory bowel diseases (e.g., ulcerative colitis, Crohn's disease, etc.), inflammatory airway disorders and diseases (e.g., asthma, chronic obstructive pulmonary disease, cystic fibrosis, etc), psoriasis, perfusion injury, restenosis, stenosis, myocardial injury, acute renal inflammation, bacterial otitis media, acute ultraviolet irradiation (e.g., sunburn), endotoxic shock, and multiple sclerosis.

BRIEF DESCRIPTION OF THE DRAWINGS

FIG. 2 shows in vitro p38 MAPK and CK1δ inhibition of enzyme activity in a concentration dependent manner. In particular, in vitro phosphorylation of a standard protein or peptide substrate by purified human p38α MAPK and CK1δ was measured in the presence of 100 mM ATP, in the absence or presence of increasing concentrations of MW01-2-069aSRM. Data are expressed as percent of the maximal enzyme activity, where enzyme activity in the absence of MW01-2-069aSRM is taken as 100%.

FIG. 4 shows oral bioavailability, safety and metabolic stability with MW01-2-069aSRM. In particular, FIG. 4A shows plasma levels after oral administration, FIG. 4B shows no liver histological toxicity screen after chronic administration, and FIG. 4C shows metabolic stability in human liver microsome screen.

DETAILED DESCRIPTION OF THE INVENTION

Figure 1:
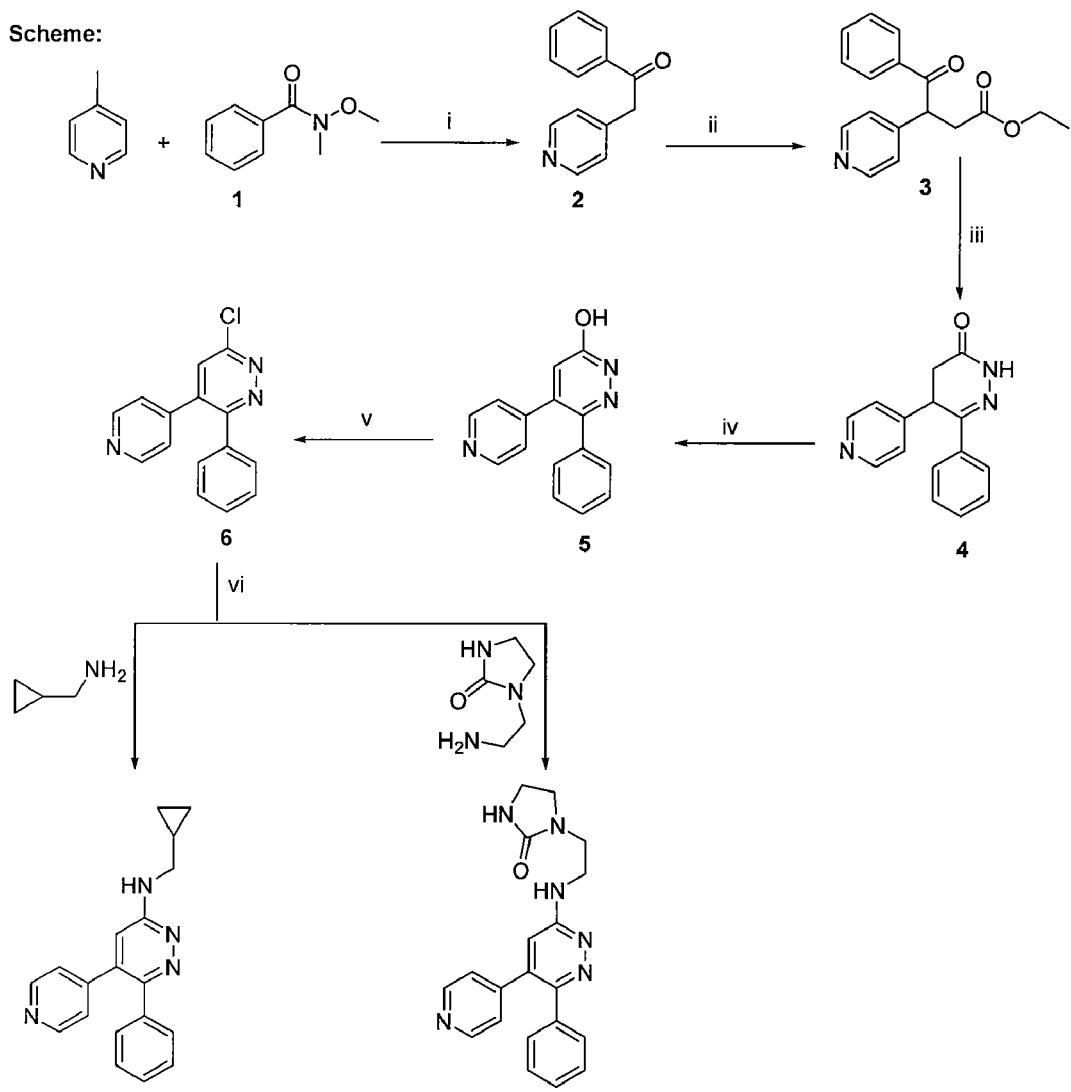
FIG. 1 shows examples of different routes of synthesis of the compounds, small molecules, and analogs thereof of the present invention.

The present invention relates to compositions and methods useful in treating diseases and disorders related to protein kinases. In particular, the present invention relates to compositions and methods useful for targeting protein kinases related to mitogen activated protein kinase (MAPK) pathways (e.g., p38 MAPK, JNK, ERK, and upstream and downstream protein kinases) and/or CK pathways (e.g., CK1δ, and upstream and downstream protein kinases), and diseases and disorders related to MAPK pathways (e.g., p38 MAPK, JNK, ERK, and upstream and downstream protein kinases) and/or CK pathways (e.g., CK1δ, and upstream and downstream protein kinases).

The mitogen activated protein kinases (MAPKs) are serine-threonine protein kinases that integrate and process extracellular stimuli through a series of intracellular signaling complexes and phosphorylation cascades that lead to stimulus-specific responses (see, e.g., Kyriakis J M and Avruch J (2001) Physiol Rev 81: 808-869; herein incorporated by reference in its entirety). In a simplest form, the MAPK cascade consists of a three-tiered series of protein kinases: a MAPK (ERKs, JNKs, p38s) and two upstream components (a MAPK kinase and a MAPKK kinase) that activate the MAPKs by a series of activating phosphorylations (see, e.g., Bonni A, et al., Science. 1999 Nov. 12; 286(5443):1358-62; Chadee D N, Mol Cell Biol. 2002 February; 22(3):737-49; Chang L, et al., Nature 2001 Mar. 1; 410(6824):37-40; Chen Y R, et al., Gene ther mol biol Vol 4, 83-98 December 1999; Hazzalin C A, et al., Nat Rev Mol Cell Biol. 2002 January; 3(1):30-40; Kato Y, et al., EMBO J. 1997 Dec. 1; 16(23):7054-66; Kiefer F, et al., EMBO J. 1996 Dec. 16; 15(24):7013-25; Pearson G, et al., J Biol Chem. 2001 Mar. 16; 276(11):7927-31; Weston C R, et al., Science. 2002 Jun. 28; 296(5577):2345-7; each herein incorporated by reference in their entireties). The activated MAPK can phosphorylate a number of substrates, including transcription factors, which then lead to stimulus-specific responses. This description of the MAPK cascades as linear, isolated pathways is understood to be oversimplified, because the MAPK pathways can interact with and be influenced by other signaling pathways, by interactions with scaffolding proteins, and by specific localizations within cells.

Protein kinases related to the MAPK pathway (e.g., p38 MAPK, JNK, ERK) are therapeutic targets for both inflammatory diseases (see, e.g., Kaminska B (2005) Biochim Biophys Acta 1754: 253-262; Kumar S, et al., Nature Rev Drug Discovery 2: 717-726; Saklatvala J (2004) Curr Opin Pharmacol 4: 372-377; each herein incorporated by reference in their entireties) and cancer (see, e.g., Engelberg D (2004)

Sem Cancer Biol 14: 271-282; Platanias L C (2003) Blood 101: 4667-4679; Rennefahrt U, et al., (2005) Cancer Lett 217: 1-9; each herein incorporated by reference in their entireties). The p38 MAPK family consists of at least four isoforms, p38α, β (and β2), δ, γ, which are encoded by separate genes, expressed in different tissues and may have distinct functions.

In terms of p38 MAPK's role in inflammatory diseases, activation of p38 MAPK has been shown to regulate gene expression and lead to increased production of proinflammatory cytokines (see, e.g., Schieven G L (2005) Curr Topics Med Chem 5: 921-928; herein incorporated by reference in its entirety). The mechanisms by which p38 MAPK stimulates proinflammatory cytokine production include phosphorylation and activation of transcription factors, some of which can increase transcription of inflammatory cytokine genes; regulation of cytokine mRNA stability and translation; and regulation of transcriptional activation of certain cytokines. Thus, p38 MAPK can modulate a number of different signaling events that can converge on proinflammatory cytokine up-regulation.

p38 MAPK has been found to be a component of tumor suppressor pathways under some conditions and as a pro-oncogenic component under other conditions (see, e.g., Engelberg D (2004) Sem Cancer Biol 14: 271-282; Rennefahrt U, et al., (2005) Cancer Lett 217: 1-9; each herein incorporated by reference in their entireties). The kinase has been shown to be involved in cell growth, differentiation, cell cycle control, and apoptosis. In certain cancers, p38 MAPK is activated and mediates cell proliferation. In addition, p38 MAPK is activated in response to environmental stresses and damaging agents, such as UV irradiation, which can induce tumors (see, e.g., Jinlian L (2007) J Biomed Sci 14: 303-312; herein incorporated by reference in its entirety).

Because of its importance in modulating proinflammatory cytokine production, p38 MAPK is a compelling therapeutic targets for small molecule development against inflammatory diseases characterized by elevated levels of proinflammatory cytokines. In addition, because of the increasing awareness of the pro-oncogenic potential of p38 MAPK and its observed effects in mediating a number of cellular processes important for cancer onset and progression, targeting p38 MAPK is a therapeutic option for treating cancer, especially for hematologic malignancies (see, e.g. Platanias L C (2003) Blood 101: 4667-4679; herein incorporated by reference in its entirety). The present invention is not limited to a particular mechanism. Indeed, an understanding of the mechanism is not necessary to practice the present invention. Nonetheless, it is contemplated that the inhibition of p38 MAPK is a useful therapy for diseases and/or disorders where p38 MAPK is over-expressed or over-activated.

CK protein kinases (e.g., CK1δ) are also serine-threonine kinases. The CK protein kinases (e.g., CK1δ) are highly conserved within their kinase domains, but differ in their N- and C-terminal non-catalytic domains (see, e.g., Knippschild U, et al., 2005, Cellular Signalling 17: 675-689; Knippschild U, et al., 2005, Onkologie 28: 508-514; each herein incorporated by reference in their entireties). The functional activity of the CK protein kinases (e.g., CK1δ) in cells can be regulated by a variety of means, including modulation of CK protein kinase (e.g., CK1δ) expression, activity, and subcellular localization. A large number of substrates for CK protein kinases (e.g., CK1δ) have been discovered, including enzymes, transcription factors, viral oncogenes, cytoskeletal proteins, membrane associated proteins, and receptors. The diversity of CK (e.g., CK1δ) substrates indicates that the enzyme is involved in regulation of diverse cellular processes.

Some examples of functions ascribed to CK protein kinases (e.g., CK1δ) include, but are not limited to, regulation of circadian rhythms through phosphorylation and modulation of the functions of specific clock proteins; involvement in cancer development through phosphorylation of the tumor suppressor p53 and the cellular oncogene Mdm2, resulting in uncontrolled cell growth, and through elevated CK (e.g., CK1δ) levels and/or activity in a variety of cancers; inhibition of apoptosis induced through different pathways, including mediating resistance of tumor cells to caspase action and interfering with retinoic acid receptor mediated apoptosis; modulation of Wnt-signaling pathways; and overexpression and involvement in neurodegenerative diseases. The present invention is not limited to a particular mechanism. Indeed, an understanding of the mechanism is not necessary to practice the present invention. Nonetheless, it is contemplated that CK protein kinases (e.g., CK1δ) are linked to various types of diseases such as cancer, inflammatory diseases, and other disorders. In addition, it is contemplated that the inhibition of CK protein kinases (e.g., CK1δ) is a useful therapy for diseases and/or disorders where CK protein kinases (e.g., CK1δ) are over-expressed or over-activated.

In some embodiments, the compositions and methods of the present invention are useful in prevention and/or treatment of diseases and/or disorders where protein kinases related to the MAPK pathway (e.g., p38 MAPK, JNK, ERK) and/or the CK pathway (e.g., CK1δ) are over-expressed or over-activated. The present invention is not limited to treating certain types of diseases and/or disorders where protein kinases related to the MAPK pathway (e.g., p38 MAPK, JNK, ERK) and/or the CK pathway (e.g., CK1δ) are over-expressed or over-activated. In some embodiments, the compositions and methods of the present invention are useful in prevention and/or treatment of inflammatory diseases that include, but are not limited to, arthritis (e.g., osteoarthritis, rheumatoid arthritis, etc.), inflammatory bowel diseases (e.g., ulcerative colitis, Crohn's disease, etc.), inflammatory airway disorders and diseases (e.g., asthma, chronic obstructive pulmonary disease, cystic fibrosis, etc), psoriasis, perfusion injury, restenosis, stenosis, myocardial injury, acute renal inflammation, bacterial otitis media, acute ultraviolet irradiation (e.g., sunburn) and endotoxic shock. In some embodiments, the compositions and methods of the present invention are useful in prevention and/or treatment of Alzheimers disease and related disorders, presenile and senile forms; amyloid angiopathy; mild cognitive impairment; Alzheimer's disease-related dementia (e.g., vascular dementia or Alzheimer dementia); AIDS related dementia, tauopathies (e.g., argyrophilic grain dementia, corticobasal degeneration, dementia pugilistica, diffuse neurofibrillary tangles with calcification, frontotemporal dementia with parkinsonism, Prion-related disease, Hallervorden-Spatz disease, myotonic dystrophy, Niemann-Pick disease type C, non-Guamanian Motor Neuron disease with neurofibrillary tangles, Pick's disease, postencephalitic parkinsonism, cerebral amyloid angiopathy, progressive subcortical gliosis, progressive supranuclear palsy, subacute sclerosing panencephalitis, and tangle only dementia), aipha-synucleinopathy (e.g., dementia with Lewy bodies, multiple system atrophy with glial cytoplasmic inclusions), multiple system atrophies, Shy-Drager syndrome, spinocerebellar ataxia (e.g., DRPLA or Machado-Joseph Disease); striatonigral degeneration, olivopontocerebellar atrophy, neurodegeneration with brain iron accumulation type I, olfactory dysfunction, and amyotrophic lateral sclerosis); Parkinson's disease (e.g., familial or non-familial); Amyotrophic Lateral Sclerosis; Spastic paraplegia (e.g., associated with defective function of chaperones and/or triple A proteins); Huntington's Disease, spinocerebellar ataxia, Freidrich's Ataxia; cerebrovascular diseases including stroke, hypoxia, ischemia, infarction, intracerebral hemorrhage; traumatic brain injury; Down's syndrome; head trauma with post-traumatic accumulation of amyloid beta peptide; Familial British Dementia; Familial Danish Dementia; Presenile Dementia with Spastic Ataxia; Cerebral Amyloid Angiopathy, British Type; Presenile Dementia With Spastic Ataxia Cerebral Amyloid Angiopathy, Danish Type; Familial encephalopathy with neuroserpin inclusion bodies (FENIB); Amyloid Polyneuropathy (e.g., senile amyloid polyneuropathy or systemic Amyloidosis); Inclusion Body myositis due to amyloid beta peptide; Familial and Finnish Type Amyloidosis; Systemic amyloidosis associated with multiple myeloma; Familial Mediterranean Fever; multiple sclerosis, optic neuritis; Guillain-Barre Syndrome; chronic inflammatory demyelinating polyneuropathy; chronic infections and inflammations; acute disseminated encephalomyelitis (ADEM); autoimmune inner ear disease (AIED); diabetes; pancreatitis; gout; artherioscierosis, inflammatory aortic aneurysm; glomerulonephritis; sacoidosis cancer; restenosis; rheumatic fever; systemic lupus erythematosus; Reiter's syndrome; psoriatic arthritis; ankylosing spondylitis; coxarthritis; pelvic inflammatory disease; osteomyelitis; adhesive capsulitis; oligoarthritis; periarthritis; polyarthritis; Still's disease; synovitis; inflammatory dermatosis; and, wound healing. In some embodiments, the compositions and methods of the present invention are useful in prevention and/or treatment of skin disorders: including ichthyosis vulgaris, atopic dermatitis, psoriasis, eczema, allergic skin disease, and hypersensitivity reactions; intestinal disorders: including inflammatory bowel disease, Crohn's disease, ulcers, bacterial infections, hemorrhagic shock, diarrhea, colitis, pancreatitis; lung disorders: including acute lung injury after infection, sepsis, thrombin-induced lung injury, lung injury after reperfusion, chronic obstructive pulmonary disease, cystic fibrosis, inflammatory airway diseases; interstitial cystitis of the bladder; coronary disease after ischemia-reperfusion injury; acute renal inflammation; bacterial otitis media; chorioretinal vascular disease; neurologic disorders: including multiple sclerosis, Alzheimer's disease, vascular dementia, traumatic brain injury, ALS, Parkinson's disease, stroke, vasogenic brain edema, meningoencephalitis, cerebral hemorrhage, Guillain-Barre syndrome; aplastic anemia; bone marrow failure syndrome; and cancers, including organ cancers such as prostate, breast, skin, brain, and hematopoietic malignancies including leukemias, lymphomas, and multiple myeloma. One skilled in the art will recognize a myriad of other disorders and diseases that would be equally preventable and/or treatable by the compositions and methods of the present invention.

In some embodiments, the present invention provides compositions comprising compounds, small molecules and/or analogs thereof useful in inhibiting protein kinase activity related to the MAPK pathway (e.g., p38 MAPK, JNK, ERK, and upstream and downstream protein kinases) and/or the CK pathway (e.g., CK1δ, and upstream and downstream protein kinases). The present invention is not limited to particular types and/or kinds of compounds, small molecules and/or analogs thereof that are useful in inhibiting protein kinase activity related to the MAPK pathway (e.g., p38 MAPK, JNK, ERK, and upstream and downstream protein kinases) and/or the CK pathway (e.g., CK1δ, and upstream and downstream protein kinases). In some embodiments, the compounds, small molecules and/or analogs thereof that are useful in inhibiting protein kinase activity related to the MAPK pathway (e.g., p38 MAPK, JNK, ERK, and upstream and downstream protein kinases) and/or the CK pathway (e.g., CK1δ, and upstream and downstream protein kinases) do not inhibit related protein kinases such as DAPK, PKC, PKA, or MLCK (e.g., as determined in a standard activity assay in vitro or in vivo).

In some embodiments, the compounds, small molecules and/or analogs thereof that are useful in inhibiting protein kinase activity related to the MAPK pathway (e.g., p38 MAPK, JNK, ERK, and upstream and downstream protein kinases) and/or the CK pathway (e.g., CK1δ, and upstream and downstream protein kinases) are described by the following structures:

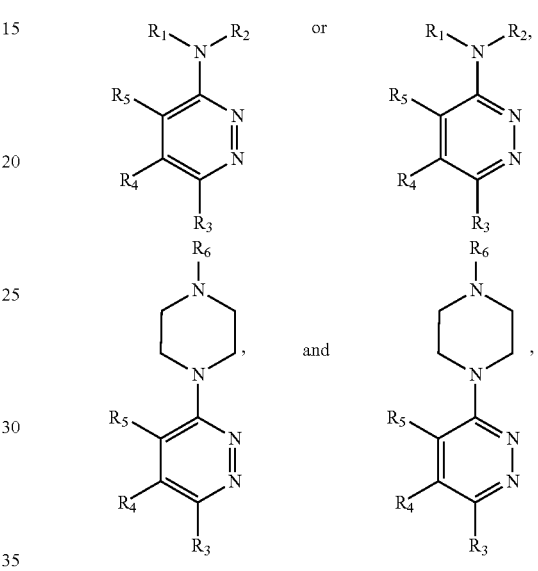

including salts and both R and S enantiomeric forms and racemic mixtures thereof; wherein R1, R2, R3, R4, and R6 are independently selected from H, C, CH, CH2, CH3,

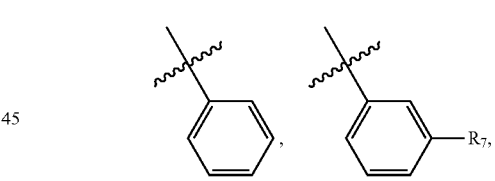

naphthalene,

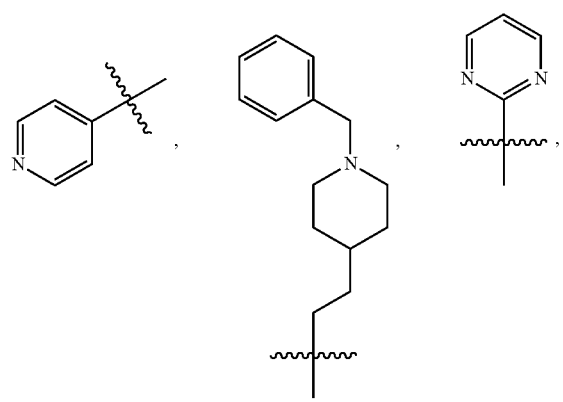

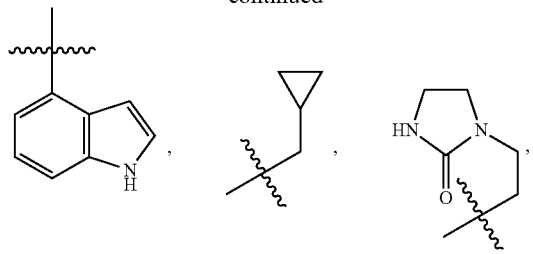

and a substituted or unsubstituted chemical moiety comprising at least one of the following: alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, carboxamide, hydrogen, amino, nitrogen, pyridine, quinoline, isoquinoline, pyrazine, quinoxaline, acridine, pyrimidine, quinazoline, pyridazine, piperazine, cinnoline, cycloaliphatic subgroup, ester, ether, sulfur, phosphorous, oxygen, an aromatic ring, a non-aromatic ring, a linear or branched, saturated or unsaturated, a substituted or unsubstituted, aliphatic chain having at least 2 carbons; wherein R5 is H, CH3, a linear or branched, saturated or unsaturated, a substituted or unsubstituted, aliphatic chain having less than 5 carbons; wherein R7 is selected from the group consisting of H, C, CH, CH2, CH3,

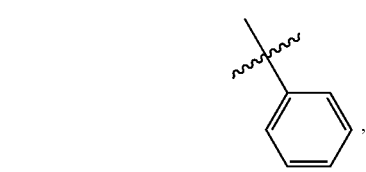

naphthalene,

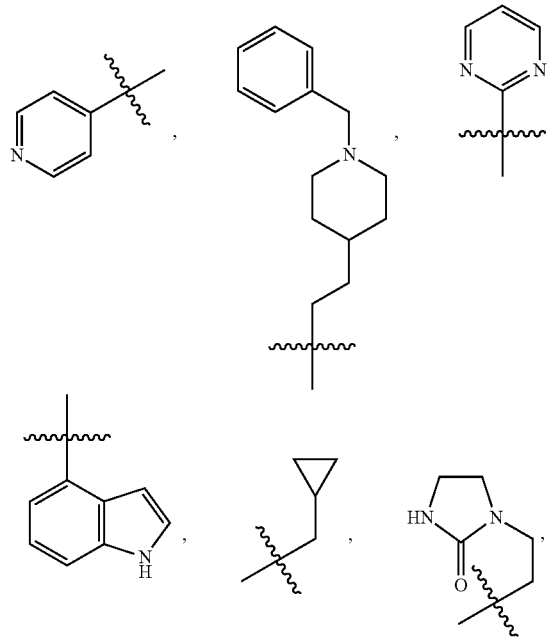

and a substituted or unsubstituted chemical moiety comprising at least one of the following: alkyl, alkenyl, alkynyl, alkylene, alkenylene, alkoxy, alkenyloxy, cycloalkyl, cycloalkenyl, aryl, aryloxy, arylalkoxy, aroyl, heteroaryl, heterocyclic, acyl, acyloxy, sulfonyl, sulfinyl, sulfenyl, imino, azido, thiol, thioalkyl, thioalkoxy, thioaryl, nitro, ureido, cyano, halo, silyl, silyloxy, silylalkyl, silylthio, =O, =S, carboxyl, carbonyl, carbamoyl, carboxamide, hydrogen, amino, nitrogen, pyridine, quinoline, isoquinoline, pyrazine, quinoxaline, acridine, pyrimidine, quinazoline, pyridazine, piperazine, cinnoline, cycloaliphatic subgroup, ester, ether, sulfur, phosphorous, oxygen, an aromatic ring, a non-aromatic ring, a linear or branched, saturated or unsaturated, a substituted or unsubstituted, aliphatic chain having at least 2 carbons.

In some embodiments, R3 is aromatic and R4 is a substituted or unsubstituted amine.

In some embodiments, the size of the R5 group is such that it does not sterically hinder the R4 group.

In some embodiments, the compound is one or more of:

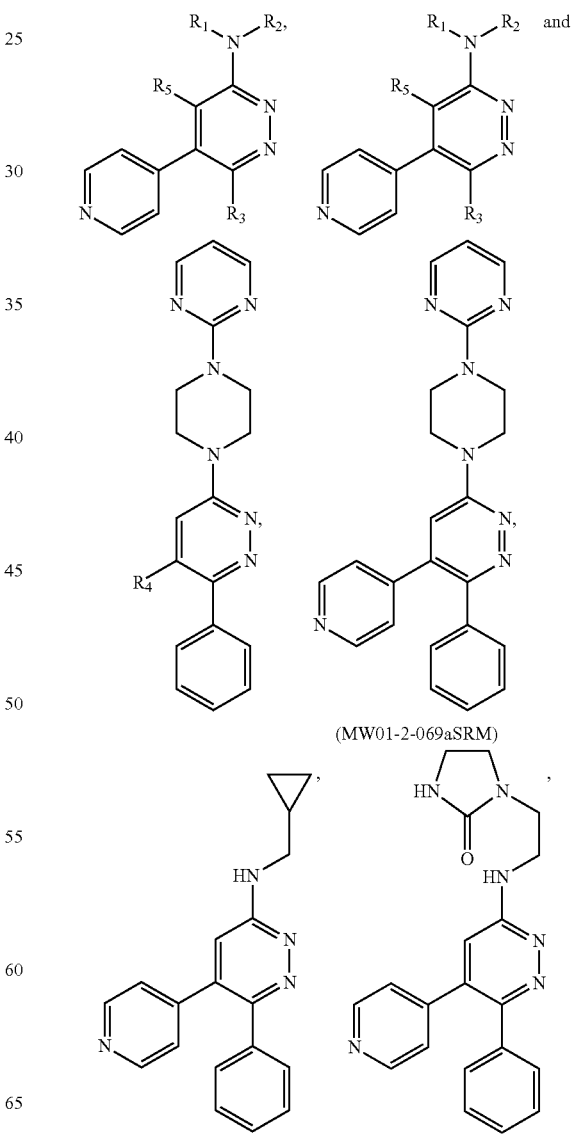

-continued

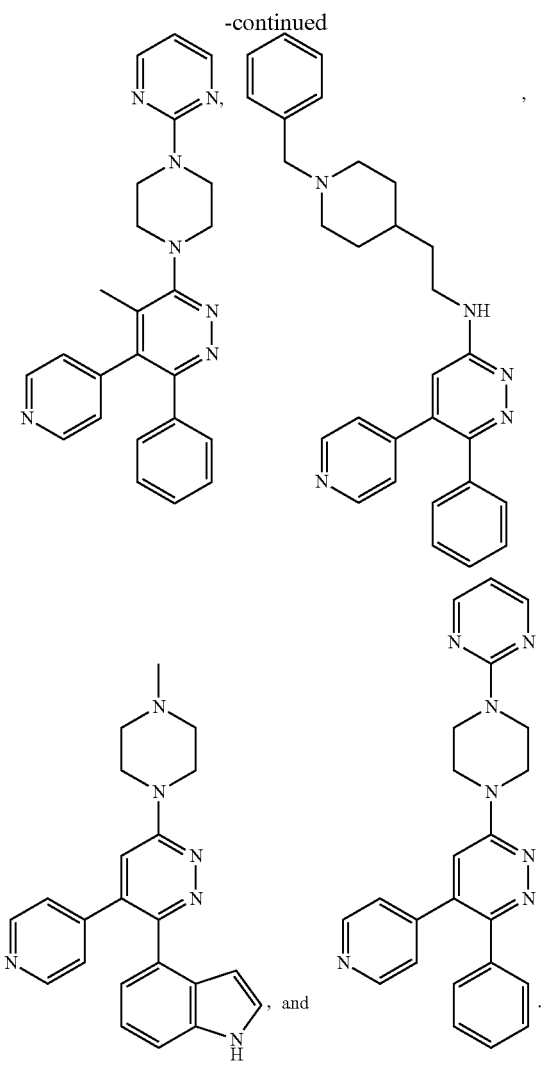

Figure 3:
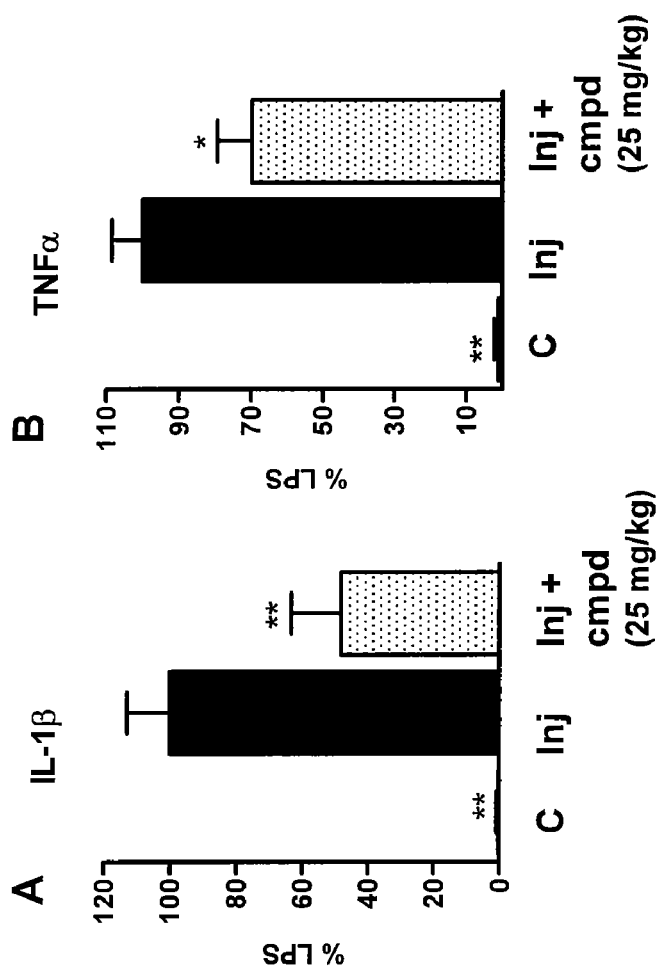
FIG. 3 shows in vivo LPS-induced serum cytokine level inhibition in an acute inflammation mouse model with MW01-2-069aSRM. MW01-2-069aSRM (25 mg/kg) was administered by oral gavage, then LPS (10 mg/kg) was given i.p. 30 minutes later. After 6 hr, serum cytokine levels were measured by ELISA. MW01-2-069aSRM was shown to be an effective p38α MAPK inhibitor.

The present invention is not limited to particular synthesis schemes for generating the compounds of the present invention. In some embodiments, the synthesis schemes depicted in FIG. 1 are used to generate the compounds of the present invention. In some embodiments, the synthesis schemes described in WO 2006/050389, herein incorporated by reference in its entirety, are utilized for generating the compounds of the present invention In some embodiments, as shown in FIG. 2, experiments conducted during the course of development of embodiments of the present invention demonstrated that MW01-2-069aSRM or analogs thereof inhibit protein kinase activity. As shown in FIG. 2, MW01-2-069aSRM was shown to inhibit in vitro p38 MAPK and CK1δ enzyme activity in a concentration dependent manner. As shown in FIG. 3, MW01-2-069aSRM was shown to inhibit LPS-induced serum cytokine levels in vivo in an acute inflammation mouse model. MW01-2-069aSRM (25 mg/kg) was administered by oral gavage, then LPS (10 mg/kg) was given i.p. 30 minutes later. After 6 hr, serum cytokine levels were measured by ELISA. MW01-2-069aSRM was shown to be an effective p38α MAPK inhibitor. As shown in FIG. 4, oral bioavailability, safety and metabolic stability is demonstrated for MW01-2-069aSRM. MW01-2-069aSRM exemplifies the activity and properties of the classes of compounds described herein.

In some embodiments, the compounds, small molecules and/or analogs thereof that are useful in inhibiting protein kinase activity related to the MAPK pathway (e.g., p38 MAPK, JNK, ERK) and/or the CK pathway (e.g., CK1δ) are administered to subjects to prevent an inflammatory disorder or disease. In some embodiments, the compounds, small molecules or analogs thereof are administered to subjects as a therapeutic to treat a subject with an inflammatory disorder or disease. In some embodiments, the compounds, small molecules or analogs thereof are administered to non-human animals useful as test subjects. In some embodiments, the compounds, small molecules or analogs thereof are administered to humans. In some embodiments, the compounds, small molecules or analogs thereof are administered to subjects in combination with other therapies.

In some embodiments, the compounds, small molecules or analogs thereof are administered to subjects in combination with anti-inflammatory agents. The present invention is not limited to particular types or amounts of anti-inflammatory agents. In some embodiments, anti-inflammatory agents include, but are not limited to, non-steroidal anti-inflammatory drugs (NSAIDs), anti-cytokines, anti-chemokines, imatinib mesylate, sorafenib, sunitinib malate, and other small molecules, drugs, compounds know in the art to inhibit inflammation or an inflammatory response.

Additionally, any one or more of the compounds, small molecules or analogs thereof can be used in combination with at least one other therapeutic agent (e.g., potassium channel openers, calcium channel blockers, sodium hydrogen exchanger inhibitors, antiarrhythmic agents, antiatherosclerotic agents, anticoagulants, antithrombotic agents, prothrombolytic agents, fibrinogen antagonists, diuretics, antihypertensive agents, ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents selected from ACE inhibitors, AT-1 receptor antagonists, ET receptor antagonists, dual ET/AII receptor antagonists, and vasopepsidase inhibitors, or an antiplatelet agent selected from GPIIb/IIIa blockers, $P2Y_1$ and $P2Y_{12}$ antagonists, thromboxane receptor antagonists, and aspirin) in along with a pharmaceutically-acceptable carrier or diluent in a pharmaceutical composition.

In certain embodiments, one or more of the compounds, small molecules or analogs thereof can be used in combination with a therapeutic agent selected from the group consisting of potassium channel openers, calcium channel blockers, sodium hydrogen exchanger inhibitors, antiarrhythmic agents (e.g., sotalol, dofetilide, amiodarone, azimilide, ibutilide, ditiazem, verapamil), antiatherosclerotic agents, anticoagulants, antithrombotic agents, prothrombolytic agents, fibrinogen antagonists, diuretics, antihypertensive agents (e.g., captopril, lisinopril, zofenopril, ramipril, fosinopril, enalapril, ceranopril, cilazopril, delapril, pentopril, quinapril, omapatrilat, gemopatrilat, losartan, irbesartan, valsartan, sitaxsentan, atrsentan), ATPase inhibitors, mineralocorticoid receptor antagonists, phospodiesterase inhibitors, antidiabetic agents, anti-inflammatory agents, antioxidants, angiogenesis modulators, antiosteoporosis agents, hormone replacement therapies, hormone receptor modulators, oral contraceptives, antiobesity agents, antidepressants, antianxiety agents, antipsychotic agents, antiproliferative agents, antitumor agents, antiulcer and gastroesophageal reflux disease agents, growth hormone agents and/or growth hormone secretagogues, thyroid mimetics, anti-infective agents, antiviral agents, antibacterial agents, antifungal agents, cholesterol/lipid lowering agents and lipid profile therapies, and agents that mimic ischemic preconditioning and/or myocardial stunning, antiatherosclerotic agents, anticoagulants, antithrombotic agents, antihypertensive agents, antidiabetic agents, and antihypertensive agents including, but not limited to, ACE inhibitors, AT-1 receptor antagonists, ET receptor antagonists, dual ET/AII receptor antagonists, and vasopepsidase inhibitors, or an antiplatelet agent (platelet inhibitor) comprising GPIIb/IIIa blockers, $P2Y_1$ and $P2Y_{12}$ antagonists, thromboxane receptor antagonists, abciximab, eptifibatide, tirofiban, clopidogrel, toclopidine, CS-747, ifetroban, and aspirin. In certain instances, the therapeutic agent is propafenone, propranolol; sotalol, dofetilide, amiodarone, azimilide, ibutilide, ditiazem, verapamil, captopril, lisinopril, zofenopril, ramipril, fosinopril, enalapril, eranopril, cilazopril, delapril, pentopril, quinapril, omapatrilat, gemopatrilat, losartan, irbesartan, valsartan, sitaxsentan, atrsentan; verapamil, nifedipine, diltiazem, amlodipine and mybefradil, digitalis, ouabain, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolatone, aplirinone, dipyridamole, cilostazol, sildenafil, ifetroban, picotamide, ketanserin, clopidogrel, picotamide, rosuvastaitin, atavastatin visastatin, questran, CP-529414, lovenox, enoxaparain dalteparinnadolol, carvedilol, albuterol, terbutaline, formoterol, salmeterol, bitolterol, pilbuterol, fenoterol, ipratropium bromide, metformin, acarbose, repaglinide, glimpepiride, glyburide, glyburide, glipizide, glucovance, troglitazone, rosiglitazone, pioglitazone, GLP-1, nefazodone, sertraline, diazepam, lorazepam, buspirone, hydroxyzine pamoate, acarbose, endostatin, probucol, BO-653, Vitamin A, Vitamin E, AGI-1067, alendronate, raloxifene, orlistate, cyclosperine A, paclitaxel, FK506, adriamycin, famotidine, rapitidine, ompeprazole, estrogen, estradiol, dipyridamole, cilostazol, sildenafil, ketanserin, taxol, cisplatin, paclitaxel, adriamycin, epothilones, carboplatin, cromolyn, nedocromil, theophylline, zileuton, zafirlukast, monteleukast, pranleukast, beclomethasone, triamcinolone, budesonide, fluticasone, flunisolidem prednisone; dexamethasone, etanercept, aspirin, indomethacin, pravastatin, simvastatin, atorvastatin, fluvastatin, cerivastatin, AZ4522, itavastatin, ZD-4522, rosuvastatin, atavastatin, visastatin, abciximab, eptifibatide, tirofiban, clopidogrel, ticlopidine, CS-747, ifetroban, aspirin; cariporide, streptokinase, reteplase, activase, lanoteplase, urokinase, prourokinse, tenecteplase, lanoteplase, anistreplase, eminase, lepirudin, argatroban, XR-330, T686, anti-α-2-antiplasmin antibody, or doesdipyridanmol.

In some embodiments, the compounds, small molecules or analogs thereof are useful in research studies, such as studying pathways associated with serine/threonine protein kinases using in vivo or in vitro assays.

In some embodiments the present invention provides methods of storage and administration of the antagonist, agent, compound, or drug in a suitable environment (e.g. buffer system, adjuvants, etc.) in order to maintain the efficacy and potency of the agent, compound, or drug such that its usefulness in treating a disease and/or disorder relating to the MAPK pathway (e.g., p38 MAPK, JNK, ERK) and/or the CK pathway (e.g., CK1δ) is maximized. For example, small molecules or compounds benefit from a storage environment free of enzymes or compounds that could cause degradation of the small molecule, chemical, or compound.

In some embodiments, it is contemplated that the antagonist, agent, compound, or drug is administered to the individual as part of a pharmaceutical or physiological composition for treating a disease and/or disorder relating to the MAPK pathway (e.g., p38 MAPK, JNK, ERK) and/or the CK pathway (e.g., CK1δ). Such a composition can comprise a small molecule and a physiologically acceptable carrier. Pharmaceutical compositions for co-therapy can further comprise one or more additional therapeutic agents. The formulation of a pharmaceutical composition can vary according to the route of administration selected (e.g., solution, emulsion, capsule). Suitable pharmaceutical carriers can contain inert ingredients that do not interact with the small molecule function and/or additional therapeutic agent(s). Standard pharmaceutical formulation techniques can be employed, such as those described in Remington's Pharmaceutical Sciences, Mack Publishing Company, Easton, Pa. The particular co-therapeutic agent selected for administration with a MAPK pathway (e.g., p38 MAPK, JNK, ERK) inhibitor and/or the CK pathway (e.g., CK1δ) inhibitor. The type inhibitor will depend on the type and severity of the disease or disorder being treated as well as the characteristics of the individual, such as general health, age, sex, body weight and tolerance to drugs.

In some embodiments the therapeutic agent is administered by any suitable route, including, for example, orally (e.g., in capsules, suspensions or tablets) or by parenteral administration. Parenteral administration can include, for example, intramuscular, intravenous, intraarticular, subcutaneous, or intraperitoneal administration. In some embodiments, the method of administration of the therapeutic agent is by direct injection into, or adjacent to, the sire of inflammation. The small molecule therapeutic agent can also be administered transdermally, topically, by inhalation (e.g., intrabronchial, intranasal, oral inhalation or intranasal drops) or rectally. Administration can be local or systemic as indicated. The preferred mode of administration can vary depending upon the particular agent chosen. A timed-release, subcutaneous mode of administration is also contemplated. For example, a therapeutic agent is inserted under the skin either by injection, and/or by placing a solid support that has been previously impregnated or which contains (e.g., a capsule) the therapeutic agent, under the skin. An effective amount of the therapeutic agent is then released over time (e.g., days, weeks, months, and the like) such that the subject is not required to have a therapeutic agent administered on a daily basis.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion (see, e.g., WO 2006/050389, herein incorporated by reference in its entirety). In other embodiments, the active ingredient is presented as a bolus, electuary, or paste, etc.

In some embodiments, tablets comprise at least one active ingredient and optionally one or more accessory agents/carriers and are made by compressing or molding the respective agents. In some embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent.

In some embodiments of the present invention, the compounds, small molecules and analogs thereof of the present invention, and other potentially useful compounds, are screened for their binding affinity to, for example, protein kinases related to the MAPK pathway (e.g., p38 MAPK, JNK, ERK) and/or the CK pathway (e.g., CK1δ). A number of suitable screens for measuring the binding affinity of drugs and other small molecules to receptors are known in the art. In some embodiments, binding affinity screens are conducted in in vitro systems. In other embodiments, these screens are conducted in in vivo or ex vivo systems.

Additional embodiments are directed to measuring expression levels (e.g., intracellular) of protein kinases related to the MAPK pathway (e.g., p38 MAPK, JNK, ERK) and/or the CK pathway (e.g., CK1δ) in cells and/or tissues to measure the effectiveness of particular contemplated methods and compounds of the present invention.

In some embodiments, structure-based virtual screening methodologies are contemplated for predicting the binding affinity of compounds of the present invention with protein kinases related to the MAPK pathway (e.g., p38 MAPK, JNK, ERK) and/or the CK pathway (e.g., CK1δ). In some embodiments, compound structures are predicted from a molecular modeling software (e.g., MacroModel).

Any suitable assay that allows for a measurement of the rate of binding or the affinity of an exemplary compound of the present invention to protein kinases related to the MAPK pathway (e.g., p38 MAPK, JNK, ERK) and/or the CK pathway (e.g., CK1δ) may be utilized. Examples include, but are not limited to, competition binding using an exemplary compound, surface plasma resonance (SPR) and radio-immuno-preciptiation assays (Lowman et al., J. Biol. Chem. 266: 10982 [1991]). Surface Plasmon Resonance techniques involve a surface coated with a thin film of a conductive metal, such as gold, silver, chrome or aluminum, in which electromagnetic waves, called Surface Plasmons, can be induced by a beam of light incident on the metal glass interface at a specific angle called the Surface Plasmon Resonance angle. Modulation of the refractive index of the interfacial region between the solution and the metal surface following binding of the captured macromolecules causes a change in the SPR angle which can either be measured directly or which causes the amount of light reflected from the underside of the metal surface to change. Such changes can be directly related to the mass and other optical properties of the molecules binding to the SPR device surface. Several biosensor systems based on such principles have been disclosed (See e.g., WO 90/05305). There are also several commercially available SPR biosensors (e.g., BiaCore, Uppsala, Sweden).

In some embodiments, compounds are screened in cell culture or in vivo (e.g., non-human or human mammals) for an ability to modulate (e.g., alter activity) protein kinases related to the MAPK pathway (e.g., p38 MAPK, JNK, ERK) and/or the CK pathway (e.g., CK1δ). Any suitable assay may be utilized, including, but not limited to, cell proliferation assays (Commercially available from, e.g., Promega, Madison, Wis. and Stratagene, La Jolla, Calif.) and cell based dimerization assays. (See e.g., Fuh et al., Science, 256:1677 [1992]; Colosi et al., J. Biol. Chem., 268:12617 [1993]). Additional assay formats that find use with the present invention include, but are not limited to, assays for measuring cellular MAPK (e.g., p38 MAPK) and/or the CK pathway (e.g., CK1δ) levels.

The present invention also provides methods of modifying and derivatizing the compositions of the present invention to increase desirable properties (e.g., binding affinity, activity, and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In other embodiments, rational design methods are used to predict and model in silico ligand-receptor interactions prior to confirming results by routine experimentation.

EXAMPLES

Example I

Compound Synthesis Schemes

FIG. 1 shows different exemplary routes of synthesis for the compounds, small molecules, and analogs thereof of the present invention.

1-Phenyl-2-(pyridin-4-yl)ethanone: (2) To a stirred solution of lithium diisopropylamide (1.5eq) in THF at −78° C. a solution of 4-picoline (1eq) in THF is added slowly. After 15 min, a solution of N-methoxy-N-methylbenzamide (1.2eq) in THF is added. The reaction mixture is allowed to warm to ambient temperature. The formation of product is monitored by HPLC. The reaction mixture is poured into a saturated aqueous sodium bicarbonate solution, then extracted with ethylacetate. The organic phase is washed with brine, dried over anhydrous magnesium sulphate and evaporated under reduced pressure to give the crude product. The crude product is then purified by flash column chromatography (25-100% EtOAc-hexane) to give the product ketone 2. Purity>90%, ESI m/z 198.18 (MH$^+$).

Ethyl 4-oxo-4-phenyl-3-(pyridin-4-yl)butanoate: (3) Sodium hydride (1.1 eq) and anhydrous THF are combined under argon at 0° C., and a solution of compound (2) (1eq) in anhydrous THF is added and stirred. A solution of ethyl bromoacetate (1.5 eq) in anhydrous THF is added, the reaction mixture stirred at ambient temperature, and the reaction progress monitored using HPLC. The reaction mixture is slowly poured into water, saturated sodium bicarbonate added, and the resulting solution extracted with ethyl acetate. The organic extracts are dried over anhydrous sodium sulphate and then concentrated under reduced pressure to give the crude product mixture. Purification by flash column chromatography (hexane:ethyl acetate 70:30) gives the product keto-ester 3. Purity>90%, ESI m/z 284.75 (MH$^+$).

6-Phenyl-5-(pyridin-4-yl)-4,5-dihydropyridazin-3(2H)-one: (4) The compound (3) (1eq) is mixed in ethanol, hydrazine (2eq) added slowly, and the resulting solution is heated under reflux with continuous stirring until completion (monitored by HPLC). The reaction mixture is cooled to ambient temperature and solvent evaporated in vacuo. Ethyl acetate is added, followed by ether, and the solution rotary evaporated to produce a foam-like solid, which can be used for the synthesis of next step without further purification. EI m/z 251.1 (M$^+$).

6-Phenyl-5-(pyridin-4-yl)pyridazin-3-ol: (5) Compound (4) in 5 ml of acetic acid is mixed gradually with. 1.5 eq bromine (in acetic acid), refluxed at 70° C., and the reaction progress monitored by HPLC until all starting material disappears. The mixture is cooled to ambient temperature, poured unto crushed ice to quench the reaction, the pH of the aqueous reaction mixture adjusted to pH 6 with 0.2 N NaOH, and the mixture extracted with ethyl acetate. The aqueous phase is dried in vacuuo and the residue extracted with ethyl acetate and dichloromethane. Final purificaiton by flash column chromatography over silica gel column, eluting with dichloromethane and MeOH (5%), affords compound 5. Purity>90%, ESI m/z 250.20 (MH$^+$).

6-Chloro-3-phenyl-4-(pyridin-4-yl)Pyridazine: (6) Compound 5 (1 eq) and POCl$_3$ (40 mmol, 10eq) are mixed, stirred at 90° C., and the reaction monitored by HPLC. The resultant mixture is poured unto crushed ice and mixed for 30 min to decompose POCl$_3$, the pH mixture adjusted 7, and the mixture is extracted with ethyl acetate and dichloromethane. The organic extracts are combined and dried over anhydrous magnesium sulfate, the solvent evaporated in vacuo and the product purified on silica gel column and eluted with (DCM:MeOH) to yield the compound 6. Purity>93%, ESI m/z 268.40 (MH$^+$).

N-(cyclopropylmethyl)-6-phenyl-5-(pyridin-4-yl)pyridazin-3-amine: Compound 6 is aminated using 9 equiv of cyclopropylmethanamine in 1-butanol at 130° C. in a pressure vessel for 21 hrs, then the reaction mixture concentrated under reduced pressure, ethylacetate added, and the mixture dried over anhydrous sodium sulphate. The crude product is purified by flash column chromatography (dichloromethane:MeOH 70:30) gives the product. Purity>98%, ESI m/z 302.37 (MH$^+$), M.P. 198.7-199.5° C.

1-(2-(6-phenyl-5-(pyridin-4-yl)pyridazin-3-ylamino) ethyl)imidazolidin-2-one: Compound 6 is aminated using 6 equiv of 1-(2-aminoethyl)imidazolidin-2-one in 1-butanol at 130° C. in a pressure vessel for 24 hrs, the mixture concentrated under reduced pressure, ethylacetate added and washed with water, then dried over anhydrous sodium sulphate. The crude product is purified by recrystallization in methanol/hexane. Purity>98%, ESI m/z 361.63, (MH$^+$), M.P. 205.5-206.7° C. (uncorrected).

Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:
1. A pharmaceutical composition comprising a pharmaceutically acceptable carrier and a protein kinase inhibitor,
   wherein said protein kinase inhibitor inhibits one or more of p38 MAPK, JNK, ERK, and CK1δ,
   wherein said protein kinase inhibitor is described by the following formula:

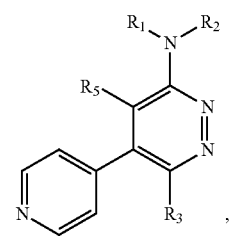

including salts and both R and S enantiomeric forms and racemic mixtures thereof;
   wherein R1 and R2 are independently selected from i) R1 is H and R2 is CH3, or ii) R1 is CH3 and R2 is H;
   wherein R3 is selected from H, CH3,

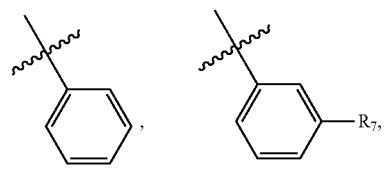

naphthalene,

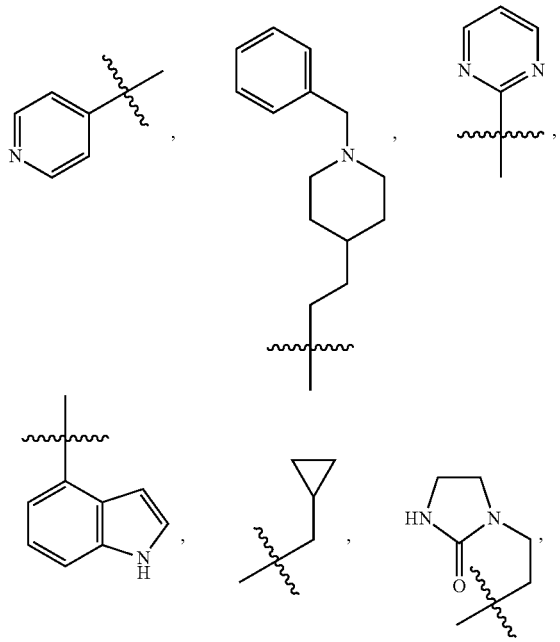

wherein R5 is H, CH3, a linear or branched, saturated or unsaturated, a substituted or unsubstituted, aliphatic chain having less than 5 carbons; and wherein R7 is selected from the group consisting of H, CH3,
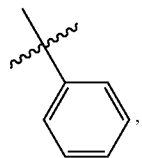
naphthalene,
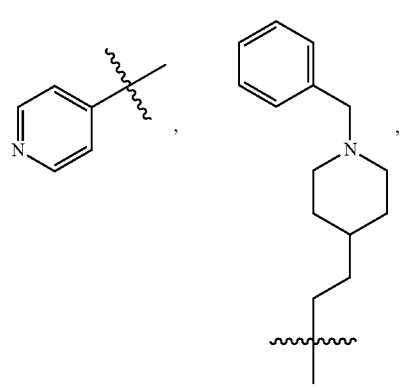
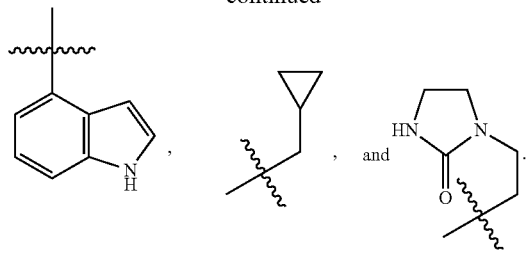
2. The pharmaceutical composition of claim 1, wherein said compound is:
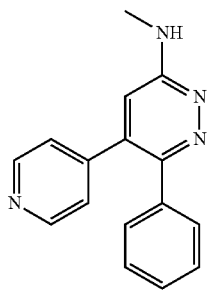 or 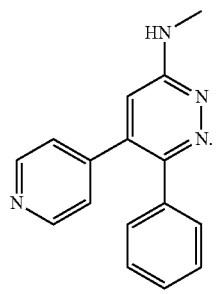
* * * * *